United States Patent [19]

Ganellin et al.

[11] 4,120,973

[45] Oct. 17, 1978

[54] IMIDAZOLYL ALKYLAMINOCYCLOBUTENEDIONES

[75] Inventors: Charon Robin Ganellin, Welwyn Garden City; Rodney Christopher Young, Bengeo, both of England

[73] Assignee: SmithKline & French Laboratories Limited, Welwyn Garden City, England

[21] Appl. No.: 833,403

[22] Filed: Sep. 15, 1977

Related U.S. Application Data

[62] Division of Ser. No. 705,216, Jul. 14, 1976, Pat. No. 4,062,863.

[30] Foreign Application Priority Data

Jul. 31, 1975 [GB] United Kingdom ............... 31971/75

[51] Int. Cl.$^2$ .................. C07D 233/64; A61K 31/415
[52] U.S. Cl. ................................. 424/273 R; 548/336
[58] Field of Search ...................... 548/336; 424/273 R

[56] References Cited

U.S. PATENT DOCUMENTS

| | | | |
|---|---|---|---|
| 3,929,765 | 12/1975 | Suzuki et al. | 548/336 |
| 4,062,967 | 12/1977 | Durant et al. | 548/342 |

OTHER PUBLICATIONS

Maahs et al. Angew. Chem. Internat. Ed. 1966, vol. 5, pp. 888–893.
Thorpe J. Chem. Soc. J. Chem. Soc. (London) B (Phys. Org.) 1968, pp. 435–436.
Griffiths et al. J. Mol. Structure 1971, vol. 8, pp. 363–371.
Neuse et al. Liebigs Ann. Chem. 1973, pp. 619–632.
Neuse et al. J. Org. Chem. 1974, vol. 39, pp. 3881–3887.
Seitz et al. Chemiker-Zeitung 1974, vol. 98, pp. 459–460.
Ried et al. Liebigs Ann. Chem. 1975, pp. 1863–1872.

*Primary Examiner*—Natalie Trousof
*Attorney, Agent, or Firm*—Joan S. Keps; Richard D. Foggio; William H. Edgerton

[57] ABSTRACT

The compounds are 1-amino-2-heterocyclic-alkylamino-cyclobut-1-ene-3,4-diones which are histamine H$_2$-antagonists.

9 Claims, No Drawings

IMIDAZOLYL ALKYLAMINOCYCLOBUTENEDIONES

This is a division of application Ser. No. 705,216 filed July 14, 1976, now U.S. Pat. No. 4,062,863.

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compound.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine is a typical example, and diphenhydramine and chlorpheniramine are other examples are mediated through histamine $H_1$-receptors (Ash and Schild, *Brit. J. Pharmac. Chemother,* 27, 427, (1966)). However, other of the biological actions of histamine are not inhibited by "antihistamines" and actions of this type which are inhibited by a compound described by Black et. al. (Nature, 236, 385 (1972)) and called burimamide are mediated through receptors which are defined by Black et. al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure.

In the treatment of certain conditions, for example inflammation and in inhibiting the actions of histamine on blood pressure, a combination of histamine $H_1$- and $H_2$-antagonists is useful.

The compounds of this invention are histamine $H_2$-antagonists. The compounds may be represented by the following general formula:

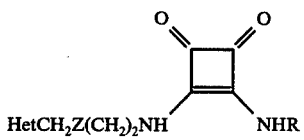

wherein R is hydrogen, lower alkyl or $(CH_2)_2Z'CH_2Het'$; Z and Z' may each be sulphur or methylene; and Het and Het' may each be an imidazole ring optionally substituted by methyl or bromo, a pyridine ring optionally substituted by hydroxy, methoxy, chloro or bromo, a thiazole ring or an isothiazole ring; or a pharmaceutically acceptable acid addition salt thereof. By the terms "lower alkyl" and "lower alkoxy" we mean alkyl and alkoxy groups containing from 1 to 4 carbon atoms.

Particularly useful compounds are those wherein Het is: 5-methyl-4-imidazolyl, 5-bromo-4-imidazolyl,3-hydroxy-2-pyridyl, 3-methoxy-2-pyridyl, 3-chloro-2-pyridyl,3-bromo-2-pyridyl, 2-thiazolyl or 3-isothiazolyl.

It is preferred that Z should be sulphur and that, when R is $(CH_2)_2Z'CH_2Het'$, Z' and Het' should be the same as Z and Het respectively i.e., so as to form a 1,2-bis compound.

Specific compounds within the scope of the present invention are:

1-amino-2-[2-((5-methyl-4-imidazolyl)methylthio)ethylamino]cyclobut-1-ene-3,4-dione and
1-methylamino-2-[2-((5-methyl-4-imidazolyl)methylthio)ethylamino]cyclobut-1-ene-3,4-dione.

The compounds of the present invention may be produced by a process which commences from an amine of Formula II:

   FORMULA II wherein Het and Z have the same significance as in Formula I. This amine is reacted with a compound of the Formula III:

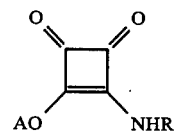   FORMULA III wherein A is lower alkyl, preferably methyl, and R has the same significance as in Formula I. The compound of Formula III wherein R is hydrogen and A is methyl is known and wherein R is other than hydrogen may be formed by reaction of the amine $RNH_2$ with the known "dialkyl squarate" of Formula IV:

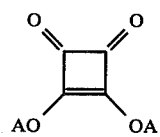   FORMULA IV wherein A is lower alkyl, preferably methyl.

The compounds of Formula I block histamine $H_2$-receptors that is they inhibit the biological actions of histamine which are not inhibited by "antihistamines" such as mepyramine but are inhibited by burimamide. For example, the compounds of this invention have been found to exhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema test, where the oedema is induced by an irritant; the rat paw volume is reduced by subcutaneous injection of doses of about 500 micromoles/Kg of a compound of Formula I. In a conventional test, such as the measurement of blood pressure in the anaesthetized rat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydroiodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula I or a pharmaceutically acceptable acid addition salt thereof and methods of blocking histamine $H_2$-receptors which comprise administering to an animal a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to block histamine $H_2$-receptors. The route of administration may be internal, for example oral or parenteral, or may be topical. Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following Examples, in which all temperatures are in degrees Centigrade.

EXAMPLE 1

1-Amino-2-[2-(4-methyl-5-imidazolylmethylthio)ethylamino]cyclobut-1-ene-3,4-dione.

A mixture of 4-methyl-5-(2-aminoethyl)thiomethyl imidazole (1.47 g) and 1-amino-2-methoxycyclobutenedione (0.72 g) was heated to 140° with stirring for 25 minutes. After allowing to cool, the resulting glass was purified on a column of silica gel, eluting with mixtures of chloroform and ethanol. The solid so obtained was recrystallised three times from ethanol to afford the title compound, m.p. 219° decomp., (0.23 g).

(Found: C, 49.1; H, 5.1; N, 20.2; S, 12.5% $C_{11}H_{14}N_4O_2S$. Requires; C, 49.6; H, 5.3; N, 21.0; S, 12.0%).

Reacting with hydrochloric acid gives the hydrochloride salt.

EXAMPLE 2

1-Methylamino-2-[2-(4-methyl-5-imidazolylmethylthio)ethylamino]cyclobut-1-ene-3,4-dione (i) Into an ethereal solution of dimethyl squarate (5.58 g) was passed methylamine gas, and the mixture was stirred for 30 minutes at room temperature. The precipitated solid was filtered off and dried, and recrystallised from methyl ethyl ketone to give 1-methylamino-2-methoxycyclobutenedione (2.40 g), m.p. 177°-178°.

(Found: C, 51.3; H, 5.0; N, 9.7% $C_6H_7NO_3$. Requires: C, 51.1; H, 5.0; N, 9.9%).

(ii) A mixture of 1-methylamino-2-methoxycyclobutenedione (1.20 g) and 4-methyl-5-[(2-aminoethyl)thiomethyl]imidazole (1.95 g) was heated to 170° with stirring for 40 minutes. After allowing to cool, the resulting glass was purified on a column of silica gel, eluting with mixtures of chloroform and ethanol. The solid so obtained was recrystallised twice from ethanol to give the title compound m.p. 207.5°-208.5°, (0.19 g).

(Found: C, 51.2; H, 5.9; N, 19.7; S, 11.4% $C_{12}H_{16}N_4O_2S$. Requires: C, 51.4; H, 5.8; N, 20.0; S, 11.4%).

Reacting with maleic acid in ethanol gives the maleate salt.

EXAMPLE 3

When in the procedure of Example 2(i), 4-methyl-5-[(2-aminoethyl)thiomethyl]imidazole is reacted with dimethyl squarate, the product is 1-methoxy-2-[2-(4-methyl-5-imidazolylmethylthio)ethylamino]cyclobut-1-ene-3,4-dione and when this is further reacted according to the procedure of Example 2(ii), the product is 1,2-bis-[2-(4-methyl-5-imidazolylmethylthio)ethylamino]cyclobut-1-ene-3,4-dione. Reacting with hydrobromic acid gives the hydrobromide salt.

EXAMPLE 4

Reaction of 1-amino-2-methoxycyclobut-1-ene-3,4-dione according to the procedure of Example 1 with the following amines:
4-bromo-5-[(2-aminoethyl)thiomethyl]imidazole,
3-methoxy-2-[(2-aminoethyl)thiomethyl]pyridine,
3-hydroxy-2-[(2-aminoethyl)thiomethyl]pyridine,
3-chloro-2-[(2-aminoethyl)thiomethyl]pyridine,
3-bromo-2-[(2-aminoethyl)thiomethyl]pyridine,
2-[(2-aminoethyl)thiomethyl]thiazole, 3-[(2-aminoethyl)thiomethyl]isothiazole and
4-(4-aminobutyl)imidazole
yields the following compounds respectively:

1-amino-2-[2-(4-bromo-5-imidazolylmethylthio)ethylamino]cyclobut-1-ene-3,4-dione,
1-amino-2-[2-(3-methoxy-2-pyridylmethylthio)ethylamino]cyclobut-1-ene-3,4-dione,
1-amino-2-[2-(3-hydroxy-2-pyridylmethylthio)ethylamino]cyclobut-1-ene-3,4-dione,
1-amino-2-[2-(3-chloro-2-pyridylmethylthio)ethylamino]cyclobut-1-ene-3,4-dione,
1-amino-2-[2-(3-bromo-2-pyridylmethylthio)ethylamino]cyclobut-1-ene-3,4-dione,
1-amino-2-[2-(2-thiazolylmethylthio)ethylamino]cyclobut-1-ene-3,4-dione,
1-amino-2-[2-(3-isothiazolylmethylthio)ethylamino]cyclobut-1-ene-3,4-dione and
1-amino-2-[4-(4-imidazolyl)butylamino]cyclobut-1-ene-3,4-dione.

EXAMPLE 5

When, in the procedure of Example 4, 1-methoxy-2-[2-(4-methyl-5-imidazolylmethylthio)ethylamino]cyclobut-1-ene-3,4-dione is used in place of 1-amino-2-methoxycyclobut-1-ene-3,4-dione the products are respectively:

1-[2-(4-methyl-5-imidazolylmethylthio)ethylamino]-2-[2-(4-bromo-5-imidazolylmethylthio)ethylamino]cyclobut-1-ene-3,4-dione,
1-[2-(4-methyl-5-imidazolylmethylthio)ethylamino]-2-[2-(3-methoxy-2-pyridylmethylthio)ethylamino]cyclobut-1-ene-3,4-dione.
1-[2-(4-methyl-5-imidazolylmethylthio)ethylamino]-2-[2-(3-hydroxy-2-pyridylmethylthio)ethylamino]cyclobut-1-ene-3,4-dione,
1-[2-(4-methyl-5-imidazolylmethylthio)ethylamino]-2-[2-(3-chloro-2-pyridylmethylthio)ethylamino]cyclobut-1-ene-3,4-dione,
1-[2-(4-methyl-5-imidazolylmethylthio)ethylamino]-2-[2-(3-bromo-2-pyridylmethylthio)ethylamino]cyclobut-1-ene-3,4-dione,
1-[2-(4-methyl-5-imidazolylmethylthio)ethylamino]-2-[2-(2-thiazolylmethylthio)ethylamino]cyclobut-1-ene-3,4-dione,
1-[2-(4-methyl-5-imidazolylmethylthio)ethylamino]-2-[2-(3-isothiazolylmethylthio)ethylamino]cyclobut-1-ene-3,4-dione and
1-[2-(4-methyl-5-imidazolylmethylthio)ethylamino]-2-[4-(4-imidazolylbutylamino]cyclobut-1-ene-3,4-dione.

EXAMPLE 6

| Ingredients | Amount |
| --- | --- |
| 1-Amino-2-[2-((4-methyl-5-imidazolyl)methylthio)ethylamino]cyclobut-1-ene-3,4-dione | 200 mg |
| Sucrose | 70 mg |
| Starch | 25 mg |
| Talc | 5 mg |
| Stearic Acid | 2 mg |

The ingredients are mixed and filled into a hard gelatin capsule.

EXAMPLE 7

| Ingredients | Amount |
| --- | --- |
| 1-Methylamino-2-[2-((4-methyl-5-imidazolyl)methylthio)ethylamino]cyclobut-1-ene-3, 4-dione | 200 mg |
| Lactose | 100 mg |

The ingredients are mixed and filled into a hard gelatin capsule.

What is claimed is:

1. A compound of the formula:

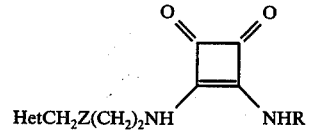

wherein R is $(CH_2)_2Z'CH_2Het'$; Z and Z' may each be sulphur or methylene; and Het and Het' may each be an imidazole ring attached at a ring carbon and optionally substituted by methyl or bromo; or a pharmaceutically acceptable acid addition salt thereof.

2. A compound according to claim 1 wherein Het is 5-methyl-4-imidazolyl or 5-bromo-4-imidazolyl.

3. A compound according to claim 1 wherein Z is sulphur.

4. A compound according to claim 1 wherein R is $(CH_2)_2Z'CH_2Het'$ and Z' and Het' are the same as Z and Het respectively.

5. A compound according to claim 1, said compound being 1,2-bis-[2-(4-methyl-5-imidazolylmethylthio)ethylamino]-cyclobut-1-ene-3,4-dione.

6. A compound according to claim 1, said compound being 1-[2-(4-methyl-5-imidazolylmethylthio)ethylamino]-2-[2-(4-bromo-5-imidazolylmethylthio)ethylamino]cyclobut-1-ene-3,4-dione.

7. A compound according to claim 1, said compound being 1-[2-(4-methyl-5-imidazolylmethylthio)ethylamino]-2-[4-(4-imidazolylbutylamino]cyclobut-1-ene-3,4-dione.

8. A pharmaceutical composition to block histamine $H_2$-receptors comprising a pharmaceutical carrier and, in an effective amount to block said receptors, a compound of claim 1.

9. A method of blocking histamine $H_2$-receptors which comprises administering to an animal in an effective amount to block said receptors a compound of claim 1.

* * * * *